US005728574A

United States Patent [19]
Legg

[11] Patent Number: 5,728,574
[45] Date of Patent: Mar. 17, 1998

[54] VIABILITY OF BACTERIAL DRIED CELLS

[75] Inventor: Michael Jeremy Legg, Reading, England

[73] Assignee: Zeneca Limited, London, England

[21] Appl. No.: 397,270

[22] PCT Filed: Jul. 19, 1994

[86] PCT No.: PCT/GB94/01556

§ 371 Date: May 12, 1995

§ 102(e) Date: May 12, 1995

[87] PCT Pub. No.: WO95/03395

PCT Pub. Date: Feb. 2, 1995

[30] Foreign Application Priority Data

Jul. 19, 1993 [GB] United Kingdom ............... 9314886

[51] Int. Cl.$^6$ ............... A01N 63/00; C12N 1/00; C12N 1/04
[52] U.S. Cl. ............... 435/260; 424/93.47; 435/243; 435/252.1; 435/253.3
[58] Field of Search ............... 435/243, 252.1, 435/253.3, 260; 424/93.47

[56] References Cited

U.S. PATENT DOCUMENTS

| 3,261,761 | 7/1966 | Anderson et al. | 195/96 |
| 5,288,634 | 2/1994 | Harman et al. | 435/254.1 |

FOREIGN PATENT DOCUMENTS 8805076  7/1988  WIPO.

OTHER PUBLICATIONS

"The Stablizing Effect of Compatible Solutes on Drying and Storage of *Escherichia Coli*," 6th European Congress on Biotechnology, Firenze, 13–17 Jun. 1993, Abs. vol. 1.

"Production of Conidial Biomass of *Trichoderma harzianum* for Biological Control," Biological Control, 1, p. 23 (1991).

"Endogenous reserves and survival of blastospores of *Beauveria bassiana* harvested from carbon– and nitrogen–limited batch cultures," Mycol. Res., 95(7), p. 821 (1991).

"Liquid Fermentation Technology for Experimental Production of Biocontrol Fungi," Phytopathology, 74(10), p. 1171 (1984).

Anders Persson et al "Physiological ...", Applied Env & Microb., Mar. 1990, pp. 686–692.

Primary Examiner—Michael G. Wityshyn
Assistant Examiner—Deborah K. Ware
Attorney, Agent, or Firm—Melissa A. Shaw

[57] ABSTRACT

The viability of bacterial cells after drying is improved by aging the culture in the stationary phase for periods of around six hours prior to drying. Further improvement may be obtained by culturing in a nitrogen deficient medium. The bacterial cells accumulate trehalose to protect the cells against drying out and other cell damage and the medium is further defined as having a higher than normal osmotic potential.

13 Claims, 4 Drawing Sheets

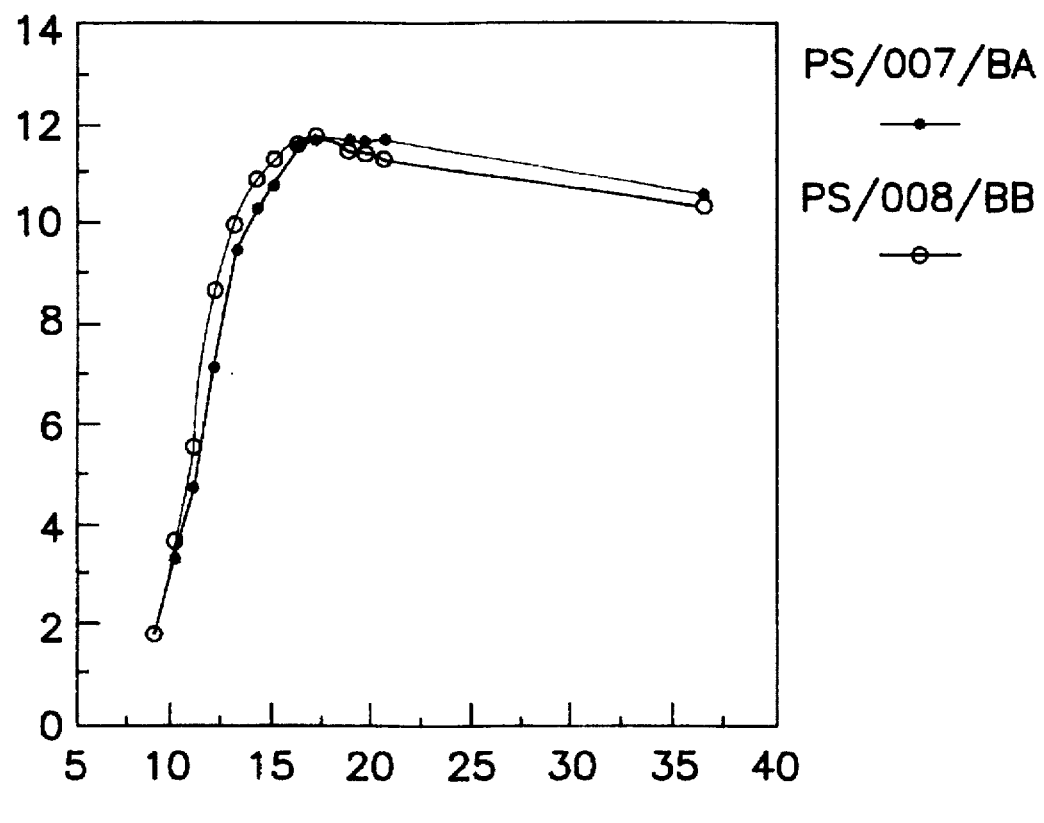

Shake Flask: 50ml in 250ml, 28°C, 200rpm

VIABILITY OF BACTERIAL DRIED CELLS

This invention relates to processes for production of a biological control agent.

Various biological organisms (including bacteria and fungi) are known to possess general or specific anti-bacterial, anti-fungal (including anti-yeast), insecticidal and/or herbicidal activity. Such organisms have enormous potential as alternatives or additions to chemical agrochemicals, and are known as biological control agents or BCAs. Numerous naturally-occurring or genetically modified biological control agents are known, and more may be discovered or developed in the future. These BCAs may be mass-produced by means of large-scale fermentation.

An obstacle to the successful commercial exploitation of biological control agents (BCAs) is their formulation, which ideally involves desiccation. Drying bacteria (such as a *Pseudomonas fluorescens* BCA) in a commercial situation leads to losses in viability which can exceed 99%. One challenge to formulation technologists is to minimise these losses.

In work leading to the present invention, we have shown that the choice of fermentation parameters can affect the eventual success of the whole formulation process.

According to the present invention, there is provided a method of improving the viability of a dried bacterial cell mass comprising maintaining a culture of bacteria in stationary phase for a period of time and thereafter drying the bacteria.

The period of time for which the culture should be maintained in stationary phase to achieve maximum viability after drying may be determined by simple testing. A period the region of six hours is generally suitable.

Preferably also the culture is conducted in a medium deficient in nitrogen.

It is also advantageous that the culture medium has a higher than normal osmotic potential.

Viability after drying may be further improved by subjecting the culture to heat shock prior to drying. Exposure to a temperature of around 37° C. for a period of from five to 15 minutes is generally suitable.

Preferably the bacterium is a Pseudomonas, more preferably *Pseudomonas fluorescens*. One particular strain of interest in this invention is *Pseudomonas fluorescens*, strain 54/96 (NCIB 40186). A culture of *Pseudomonas fluorescens*, strain 54/96 was deposited on Sep. 1, 1989 under the terms of the Budapest Treaty with the National Collection of Industrial and Marine Bacteria Limited, 23 St. Marcer Road, Aberdeen AB2 1RY United Kingdom, under the Accession Number 40186.

The production process of the invention pre-conditions the BCA to withstand drying processes that are an integral part of formulation of the product. The enhanced viability of the BCA improves the efficiency and effectiveness of the formulation process.

One or more of the following fermentation parameters are required for preconditioning the cells of the biological control agent:

(1) GROWTH PHASE

Drying survival depends on culture age. Maximum survival is achieved with stationary phase cultures (i.e. when the cells are starved of some nutrient). There is a dramatic improvement in survival at the critical point when cells enter stationary phase and an optimum survival after some period within the stationary phase (for example, at around 6 hours into stationary phase).

(2) NUTRIENT STARVATION

Nitrogen starved cells survive drying better than carbon starved cells.

(3) HEAT SHOCK

Cultures subjected to a short period of heat shock immediately prior to drying survive better. This increase in survival is particularly marked in log phase cultures but also occurs in stationary phase cultures.

(4) OSMOADAPTATION

Cells grown in media of high osmotic potential (for example, TSB with added NaCl, 0.5M) are shown to accumulate the sugar trehalose. Trehalose is known to have a protectant effect against desiccation and heat damage in many biological systems. Cells grown in this way have improved thermotolerance which may give an advantage in a drying process.

It is possible to apply one of more of the treatments listed in (1) to (4) above synergistically in a fermentation process to increase drying survival. For example, the BCA may be grown in a nitrogen-limited medium until in stationary phase (preferably well into stationary phase, for example six hours) and then heat shocked for 5–15 minutes prior to drying: this should give maximum drying survival.

By way of example only, we describe a process for production by fermentation of a *Pseudomonas fluorescens* strain for use as a biological control agent (BCA). The following Examples use the biological control agent *Pseudomonas fluorescens* strain 54/96 (NCIMB 40186) as described in International Application Publication Number WO91/05475.

Experiments investigating the effect of fermentation parameters have been carried out. Cells were grown in fermenters on tryptone soya broth (TSB) with and without various defined supplements and subjected to sublethal stresses before air drying on glass beads.

All experiments were done using laboratory scale (131 volume) fermentation. The base medium was Tryptone Soya Broth (TSB). TSB contains in 1 liter: 17 g tryptone (pancreatic digest of casein); 3 g soytone (papaic digest of soybean meal); 2.5 g dextrose; 5 g sodium chloride; 2.5 g dipotassium phosphate. TSB (C-limited) was supplemented with various media components to achieve increased drying survival.

Drying survival was measured primarily using a glass bead test, although this is not a commercial process. Some data is presented on the effect of preconditioning using nitrogen starvation on the survival of *P fluorescens* in a laboratory scale spray dryer.

Stationary phase cells survived better than growth phase cells; a sharp increase was observed at the transition point with optimum survival six hours into stationary phase.

Stationary phase cells grown in N-limiting media showed 5–20 fold better survival than stationary phase cells grown in TSB which is C-limiting (both on the bead test and in a laboratory spray dryer).

Short periods of heat shock (37° C. for 5–10 minutes) resulted in enhanced survival although this was more pronounced in the otherwise susceptible log phase cultures (95 fold increase) than in stationary phase cultures (3 fold increase).

These data suggest that a fermentation process giving maximum drying survival would involve growth of *P fluo-*

*rescens* in a medium of TSB supplemented for nitrogen limitation (recipe below) until 6 hours into stationary phase followed by heat shock for 5–10 minutes prior to drying.

It will be apparent to one skilled in the art that the processes described herein by way of example must be scaled-up for use in the commercial production of BCAs. This will involve a certain degree of optimisation to determine the exact parameters suitable for large-scale fermentation. However, the general principles of the invention (conditions or treatments which cause physiological adaptation such that cells are more able to withstand drying) are clearly applicable to small- or large-scale fermentation.

In a preferred embodiment, therefore, the present invention provides a method of producing a dried viable cell mass of *Pseudomonas fluorescens* comprising culturing the said *P. fluorescens* in stationary phase in a nitrogen-deficient medium, isolating the cultured cells and drying same. Preferably the culture is subjected to heat shock prior to drying.

The invention will now be described by way of example only with reference to the following drawings, wherein:

FIG. 1 is the growth curve of *Pseudomonas fluorescens* strain 54/96;

EXAMPLE 1

DRYING AND CELL VIABILITY

Figure 2A:
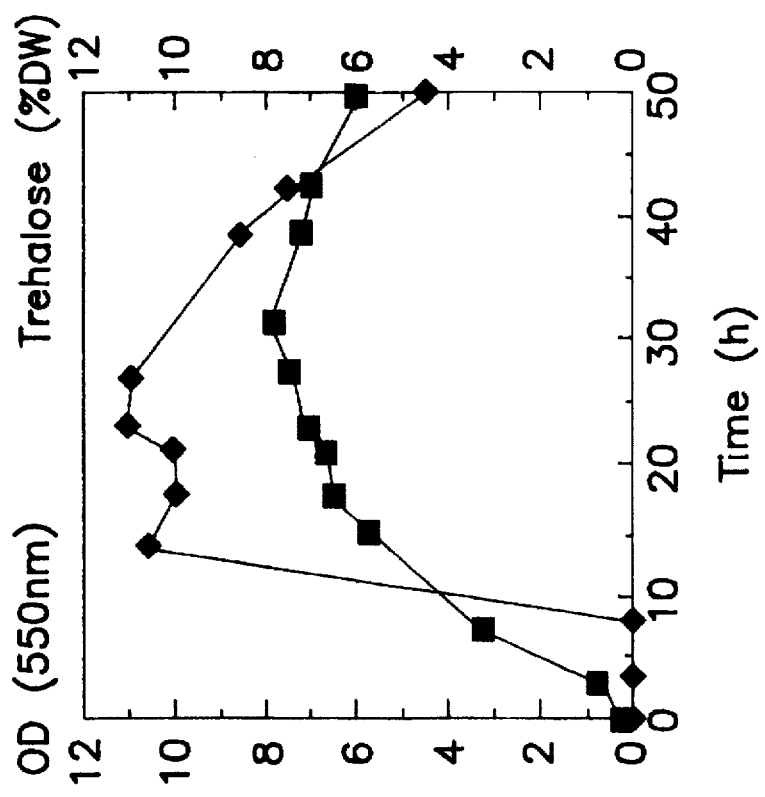
FIGS. 2A and 2B are graphs showing the intracellular accumulation of trehalose in TSB culture and TSB culture amended with 0.5M NaCl respectively.

Cell samples were dried by coating onto glass beads in a dish which was left static for up to 5 days at 20° C. Beads were sampled over a 5 day period, washed in sterile distilled water (SDW), diluted serially, and plated on Tryptone soya agar (TSA) using spread plate or Spiral Plater. Plates were incubated in the dark at 28° C. for 24 h.

EXAMPLE 2

FERMENTATION

Fermenters used were Braun Biostat E, with a total volume of 18.3 l. Standard fermenter parameters were: Temperature controlled at 25° C.; Dissolved Oxygen Tension (DOT) controlled at 50% by stirrer speed and valve setting; pH controlled at 7.0 using 2M $H_2SO_4$ and 4M NaOH; antifoam controlled by additions of polypropylene glycol MW2025 (PPG 2025). Medium was Tryptone Soya Broth (TSB) except where stated. Working volume was 13 l and a 24 h shake flask culture was used to inoculate at 0.1%.

2.1 GROWTH

Biomass was routinely measured as optical density at 550 nm wavelength ($OD_{550}$) in a Corning 258 spectrophotometer. The growth curve in a Braun Biostat was defined (FIG. 1): maximum specific growth rate ($\mu_{max}$) estimated as 0.87; Doubling time($t_d$)=47 m; Growth yield=12 ODs.

2.2 BCA ACTIVITY

BCA activity of fermenter grown culture applied as a drench was compared to shake flask culture in a standard pot test for BCA activity. 11 h (log phase) and 35 h (stationary phase) fermenter cultures plus 24 h shake flask cultures were compared. No significant difference in control of *Pythium ultimum* was observed.

EXAMPLE 3

TREHALOSE ACCUMULATION AND LOSS

Cell samples were extracted for sugar analysis. Shake flask samples were spun down (15 mins, 3,000 rpm, 4° C. in Sorval RT6000B) washed in an isotonic NaCl solution spun again and re-suspended in 70% ethanol. This suspension was sonicated (24 microns in a Soniprep 150) until total cell disruption and the cellular matter removed by centrifugation.

Analysis of intracellular extracts was by HPLC. Samples were deionised on Amberlite MB-3, dried by vacuum centrifugation (3,000 rpm, overnight in a Uniscience Univap). Dried samples were resuspended in deionised water filtered through 0.45 μm PVDF filters (Gelman Acrodisc).

Samples were analysed by HPLC (Waters Differential Refractometer Sugar Analyzer). Samples were run through filtered deionised water, with or without 5 mg/l $Ca^{2+}$EDTA, at 80° C. with a flow rate of 0.5 ml/min. The column was an Aminex HPX-42C (Biorad) and peak integration was on an IBM VG Data Systems-Minichrom v1.62)

Figure 2B:
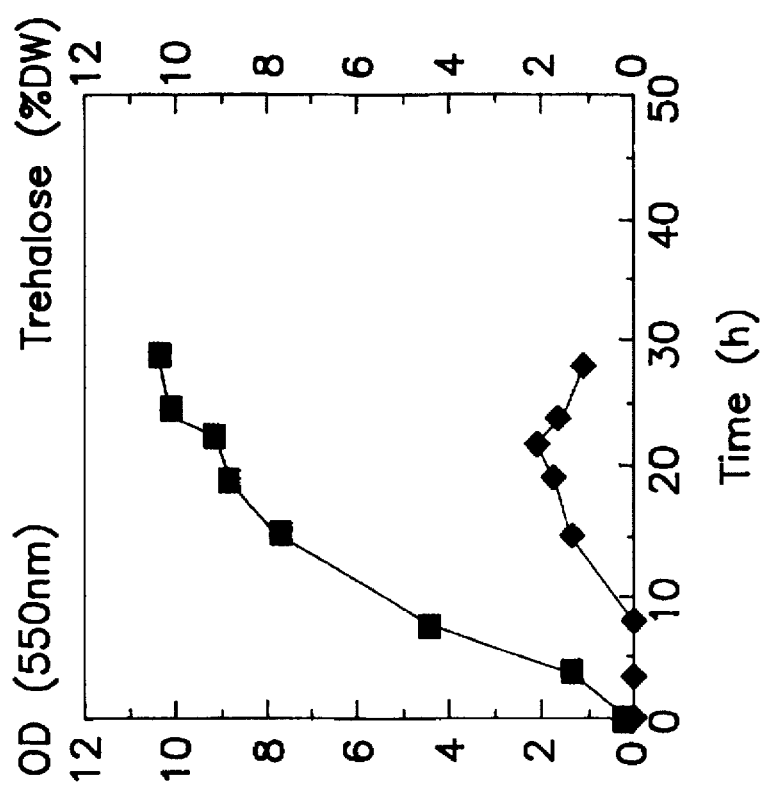

The predominant intracellular sugar was trehalose. In TSB cultures trehalose accumulated to a maximum of 2% of cell dry weight. In TSB amended with 0.5M NaCl trehalose accumulated to 11% of cell dry weight. Maximum trehalose content was found towards the end of the growth phase with a decline during stationary and decline phase (FIGS. 2A and 2B).

Cells harvested from TSB+NaCl were resuspended in either water or isotonic NaCl solution. At intervals after resuspension cells were rapidly separated by centrifugation and both cells and supernatant analysed for trehalose. Cells washed in deionised water rapidly lost trehalose to the supernatant.

3.4. THERMOTOLERANCE OF TREHALOSE ACCUMULATING CELLS

Cell samples grown under osmotic stress were incubated at 50° C. before and after washing in sterile distilled water. Unwashed 'stressed' cells displayed greater thermotolerance than washed 'stressed' cells. It is not clear from the current data whether stressed cells are significantly more thermotolerant than unstressed cells.

Cells cultured to accumulate trehalose retained their via ability better in an accelerated shelf-life study.

Cells were grown in TSB with and without NaCl. These cells were vacuum dried in the presence of formulation additives and varying concentration of NaCl. Samples of formulated material were stored at 37° C. and tested for viability over a period of 76 days.

Figure 4:
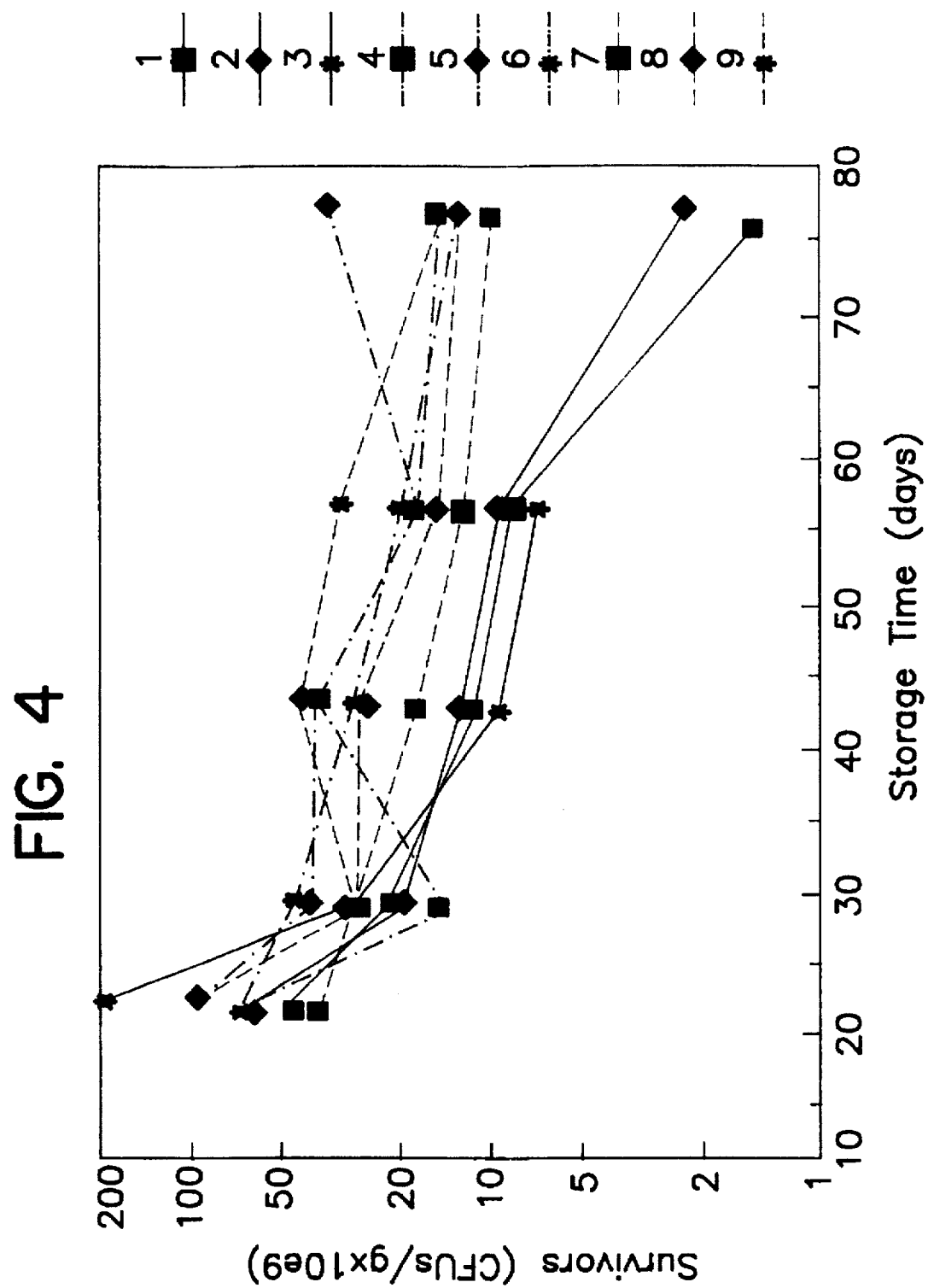
FIG. 4 is a graph illustrating the effect of trehalose on the stability of formulations.

Referring to FIG. 4, samples formulated using cells grown in TSB (nos. 1, 2 and 3) showed a more rapid decrease in viability over 76 days. Samples formulated using cells grown in TSB+0.25M NaCl (7, 8 and 9) to accumulate trehalose showed a slower decrease in viability. Samples 1,4 and 7 were formulated with additives in water: samples 2, 5 and 8 were formulated with additives in 0.25M NaCl: samples 3, 6 and 9 were formulated in 0.5M NaCl.

EXAMPLE 4

HEAT SHOCK

4.1 TEMPERATURE PROFILE

Growth rates were determined over a temperature range of 20° C. to 37° C. in TSB shake flasks. Optimum growth temperature was estimated at 28°–29° C. (µ=0.72). Growth rate at 37° C. was slow (µ=0.13); *P fluorescens* is known not to grow at 41° C., a diagnostic characteristic. Rapid cell death occurs at 50° C.

4.2 HEAT TREATMENT OF GROWING CELLS

Fermenter cultures were allowed to grow to late log phase at 21° C. The temperature was raised rapidly (−3° C. min$^{-1}$) to 37° C. and held there. Samples were taken immediately prior to the temperature shift and at intervals throughout. Samples were tested for drying survival.

Heat-shocked samples showed increases in survival up to 95× the pre-shock sample. The effect of heat-shock duration under these conditions has been examined in a number of experiments. The data shows an optimum exposure of 10–15 mins with some variation between experiments. There is evidence that the more severe the drying (i.e. longer incubation on the beads and hence lower moisture content) the smaller the effect. There is also some evidence to suggest that this decline in effect can be off-set to some extent by increasing the heat exposure.

4.3 HEAT TREATMENT OF STARVED (STATIONARY PHASE) CELLS

Cells in stationary phase survive drying much better than those in the growth phase; this will be dealt with below. Thus stationary phase cultures were heat shocked and tested for drying survival. The conditions were the same as in 4.2 except the cultures were 20–24 h old (a few hours into stationary phase).

Some reproducible but limited increase in survival could be achieved using short periods of heat exposure (5–10 mins) with mild drying (24 h). The maximum effect was a 3-fold increase. This effect is reduced with longer drying times. Also, longer exposure to the heat-shock has a detrimental effect on survival.

4.4 GEL ANALYSIS OF HEAT SHOCK PROTEINS(HSPs)

Cell samples from the heat-shock experiments were analysed for intracellular protein content by polyacrylamide gel electrophoresis (PAGE).

At least 6 different proteins were shown to accumulate during heat-shock of growing cells. There was no detectable protein accumulation in heat-shocked stationary phase cells.

EXAMPLE 5

STARVATION

5.1 COMPLEX MEDIA

Figure 3:
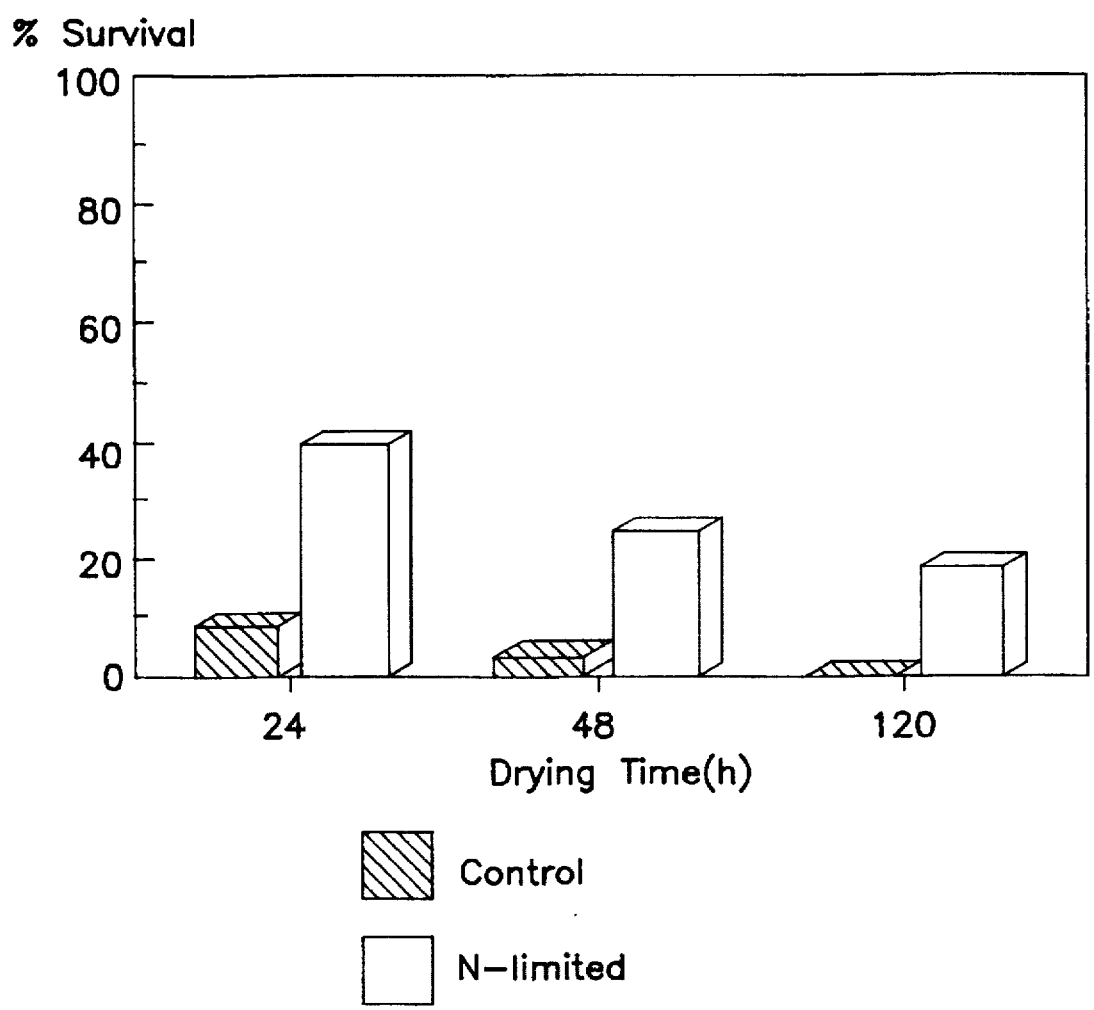
FIG. 3 shows the drying survival in N-limited media.

Drying survival was related to growth phase of cultures growing on TSB in fermenters. Samples taken at time intervals during the fermentation were subjected to the bead test. There was a dramatic increase in survival rate at the transition between growth phase and stationary phase. Optimum survival occurred 6 hours into stationary phase (FIG. 3).

5.2 NITROGEN LIMITATION

Growth of *P fluorescens* in TSB is carbon limiting (C-limiting) i.e. stationary phase cells are starved of carbon. TSB was supplemented with varying concentrations of glucose, $KH_2PO_4$ and $MgSO_4$ in a constant ratio of 25:5:1 in an attempt to achieve N-starvation. Supplementation with 20 g/l glucose showed clear increases (2/3×) in bead test survival at all incubation times over a TSB control. Cultures were not apparently N-limited (no increase in OD after addition of $NH_4Cl$).

With the higher levels of supplementation (40 g/l glucose), in the Biolab fermenters, N-limitation was achieved with a concomitant 5–8 fold increase in survival over the control (PS/073,074). An attempt to repeat this in Biostat fermenters failed to show an increase in survival on the bead test. This material was also spray dried with, again, no difference from the control (PS/091,092). Problems with the N-limited fermentation were identified as a possible cause of failure including temporary fall in pH to pH6, temporary fall in DOT and addition of excessive antifoam.

Confirmation of this result was achieved in the 20 liter fermenters Drying survival on beads was clearly better with the N-limited culture. The data suggests improvements in % survival of 5–20 (FIG. 3) fold although the variability was high. Harvest time was more clearly defined than in previous experiments and was estimated at 4–5 hours into stationary phase for both fermentations. NB: it was more difficult to estimate this in the supplemented culture because the transition from growth to stationary was more gradual—this is typical.

Washed and unwashed samples were spray dried. There was no significant difference in total CFUs recovered. However approximately 65% of unwashed N-limited cells and 35% of the washed was lost in the spray dryer due to sticking. Cell viability in terms of CFUs/g powder from 20 g wet weight starting material was of the order of 3-fold more for the N-limited samples. However recovery was low, although there was some evidence that this was improved by washing in SDW.

TABLE 1

| Fermenter | Treatment | Product Viability (CFU/g) | Recovery (grams) |
| --- | --- | --- | --- |
| C-limited | Unwashed | 1.1 × 10$^{10}$ | 20.5 |
|  | Washed | 2.7 c 10$^{10}$ | 17.9 |
| N-limited | Unwashed | 7.3 × 10$^{10}$ | 8.5 |
|  | Washed | 5.6 × 10$^{10}$ | 13.2 |

I claim:

1. A method for improving the viability of a dried bacterial cell mass consisting of *Pseudomonas fluorescens* bacteria, the method comprising the steps of:

a) culturing the *Pseudomonas fluorescens* bacteria in a nitrogen deficient medium having an osmotic potential whereby trehalose accumulates in the cells to protect the cells against desiccation and heat damage;

b) maintaining the bacteria in a stationary phase for at least six hours; and c) drying the bacteria.

2. The method of claim 1, in which the bacterium is *Pseudomonas fluorescens*, strain 54/96 (NCIB 40186).

3. The method of claim 1 in which the culturing of step (a) is conducted in a medium consisting essentially of tryptone soya broth containing 0.5M sodium chloride.

4. The method of claim 1 which comprises the additional step of subjecting the bacteria to heat shock prior to drying.

5. The method of claim 4, in which the said heat shock consists of holding the culture at a temperature of around 37° C. for a period of from five to 15 minutes.

6. The method of claim 1 in which the medium comprises tryptone soya broth.

7. The method of claim 6 in which the medium further comprises sodium chloride.

8. A method for improving the viability of a dried bacterial cell mass consisting of *Pseudomonas fluorescens* bacteria, the method comprising the steps of:
   a) culturing the *Pseudomonas fluorescens* bacteria in a medium having an osmotic potential whereby trehalose accumulates in the cells to protect the cells against desiccation and heat damage;
   b) maintaining the bacteria in a stationary phase for at least six hours;
   c) subjecting the bacteria to heat shock; and
   d) drying the bacteria.

9. The method of claim 8 in which the culturing is conducted in a medium consisting essentially of tryptone soya broth containing 0.5M sodium chloride.

10. The method of claim 8 in which said heat shock consists of holding the culture at a temperature of around 37° C. for a period of from 5 to 15 minutes.

11. The method of claim 8 in which the bacterium is *Pseudomonas fluorescens*, strain 54/96 (NCIB 40186).

12. The method of claim 8 in which the medium comprises tryptone soya broth.

13. The method of claim 12 in which the medium further comprises sodium chloride.

* * * * *